United States Patent
Alarcon et al.

(10) Patent No.: US 7,792,561 B2
(45) Date of Patent: *Sep. 7, 2010

(54) FIBER OPTIC DEVICE FOR SENSING ANALYTES

(75) Inventors: Javier Alarcon, Durham, NC (US); Kristin Weidemaier, Raleigh, NC (US); Terry J. Amiss, Cary, NC (US); John D. Denuzzio, Chapel Hill, NC (US); Christopher C. Herdman, Durham, NC (US); Ross Wayne Jacobson, Hillsborough, NC (US); J. Bruce Pitner, Durham, NC (US); Douglas B. Sherman, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/840,069

(22) Filed: Aug. 16, 2007

(65) Prior Publication Data

US 2008/0198358 A1 Aug. 21, 2008

Related U.S. Application Data

(63) Continuation of application No. 10/721,797, filed on Nov. 26, 2003.

(51) Int. Cl.
*A61B 5/145* (2006.01)
(52) U.S. Cl. ........................... 600/317; 600/310
(58) Field of Classification Search ............... 600/317, 600/322, 341, 342
See application file for complete search history.

(56) References Cited

U.S. PATENT DOCUMENTS

| 4,548,907 A | 10/1985 | Seitz et al. |
| 4,907,857 A | 3/1990 | Guilani et al. |
| 4,925,268 A | 5/1990 | Iyer et al. |

(Continued)

FOREIGN PATENT DOCUMENTS

EP 0481740 4/1992

(Continued)

OTHER PUBLICATIONS

Ballerstadt, et al., (1997) Competitive-Binding Assay Method Based on Fluorescence Quenching of Ligands Held In Close Proximity by a Multivalent Receptor. Anal. Chim. Acta 345:203-12.

(Continued)

*Primary Examiner*—Eric F Winakur
*Assistant Examiner*—Etsub D Berhanu
(74) *Attorney, Agent, or Firm*—Morgan, Lewis & Bockius LLP (57) ABSTRACT

A device for sensing analyte concentration, and in particular glucose concentration, in vivo or in vitro is disclosed. An optical conduit, preferably an optical fiber has an optical system at the proximal end of the optical conduit. A sensing element is attached to the distal end of the optical conduit, and comprises at least one binding protein adapted to bind with at least one target analyte. The sensing element further comprises at least one reporter group that undergoes a luminescence change with changing analyte concentrations. Optionally, the sensing element includes reference groups with luminescence properties that are substantially unchanged by variations in the analyte concentrations.

8 Claims, 8 Drawing Sheets

Biosensor

2 = optical system
3 = computer/microprocessor
4 = optical conduit
5 = disposable tip
6 = sensing element

U.S. PATENT DOCUMENTS

| | | | |
|---|---|---|---|
| 4,981,779 | A | 1/1991 | Wagner |
| 5,001,054 | A | 3/1991 | Wagner |
| 5,104,959 | A * | 4/1992 | Hess et al. .................... 528/79 |
| 5,127,405 | A | 7/1992 | Alcala et al. |
| 5,143,066 | A | 9/1992 | Komives et al. |
| 5,154,890 | A | 10/1992 | Mauze et al. |
| 5,219,527 | A | 6/1993 | Hui et al. |
| 5,341,805 | A | 8/1994 | Stavridi et al. |
| 5,342,789 | A | 8/1994 | Chick et al. |
| 5,377,676 | A | 1/1995 | Vari et al. |
| 5,496,997 | A | 3/1996 | Pope |
| 5,552,272 | A | 9/1996 | Bogart |
| 5,569,911 | A | 10/1996 | Tomlinson et al. |
| 5,605,152 | A | 2/1997 | Slate et al. |
| 5,626,134 | A | 5/1997 | Zuckerman |
| 5,628,310 | A | 5/1997 | Rao et al. |
| 5,700,897 | A | 12/1997 | Klainer et al. |
| 5,747,349 | A | 5/1998 | Van Den Engh et al. |
| 5,866,433 | A | 2/1999 | Schalkhammer et al. |
| 5,900,512 | A | 5/1999 | Seifert et al. |
| 5,946,083 | A | 8/1999 | Melendez et al. |
| 6,024,923 | A | 2/2000 | Melendez et al. |
| 6,040,194 | A | 3/2000 | Chick et al. |
| 6,045,756 | A | 4/2000 | Carr et al. |
| 6,081,736 | A | 6/2000 | Colvin et al. |
| 6,111,248 | A | 8/2000 | Melendez et al. |
| 6,157,442 | A | 12/2000 | Raskas |
| 6,191,847 | B1 | 2/2001 | Melendez et al. |
| 6,197,257 | B1 | 3/2001 | Raskas |
| 6,197,534 | B1 | 3/2001 | Lakawicz et al. |
| 6,256,522 | B1 | 7/2001 | Schultz |
| 6,277,627 | B1 | 8/2001 | Hellinga |
| 6,289,229 | B1 | 9/2001 | Crowley |
| 6,304,766 | B1 | 10/2001 | Colvin |
| 6,330,464 | B1 | 12/2001 | Colvin et al. |
| 6,432,723 | B1 | 8/2002 | Plaxco et al. |
| 6,512,939 | B1 | 1/2003 | Colvin et al. |
| 6,535,753 | B1 | 3/2003 | Raskas |
| 6,704,587 | B1 | 3/2004 | Krishna et al. |
| 2002/0026108 | A1 | 2/2002 | Colvin |
| 2002/0043651 | A1 | 4/2002 | Darrow et al. |
| 2002/0058863 | A1 | 5/2002 | Petersson et al. |
| 2002/0193672 | A1 | 12/2002 | Walsh et al. |
| 2003/0130167 | A1 | 7/2003 | Pitner et al. |
| 2003/0130569 | A1 | 7/2003 | Raskas |
| 2003/0134346 | A1 | 7/2003 | Amiss et al. |
| 2003/0135333 | A1 | 7/2003 | Gregory et al. |
| 2003/0153026 | A1 | 8/2003 | Alarcon et al. |
| 2003/0232383 | A1 | 12/2003 | Daunert et al. |

FOREIGN PATENT DOCUMENTS

| | | |
|---|---|---|
| WO | WO 2000/74763 A | 12/2000 |
| WO | 3060464 | 7/2003 |
| WO | WO 2004/044557 A | 5/2004 |

OTHER PUBLICATIONS

Blair, et al., (1994) Fiber Optic Sensor for Ca+ Based on an Induced Change in the Conformation of the Protein Calmodulin. Anal Chem., 66:300-2.

De Lorimier, et al., (2002) Construction Of A Fluorescent Biosensor Family. Protein Sci. 11:2655-75.

Gilardi, et al., Engineering the Maltose Binding Protein For Reagentless Fluorescence Sensing (1994) Anal. Chem., 66:3840-47.

Hellinga, et al., (1998) Protein Engineering And The Development Of Generic Biosensors. Trends Biotechnol. 16:183-89.

Russell, et al., (1999) a Fluorescence-Based Glucose Biosensor Using Concanavalin A And Dextran Encapsulated In a Poly(Ethylene Glycol) Hydrogel. Anal. Chem. 71:3126-32.

Salins, et al., (2001) A Novel Reagentless Sensing System for Measuring Glucose Based On The Galactose/Glucose-Binding Protein. Anal Biochem. 294:19-26.

Shilton, et al., (1996) Conformational Changes of Three Periplasmic Receptors For Bacterial Chemotaxis And Transport: The Maltose-, Glucose/Galactose- And Ribose-Binding Proteins. J. Mol. Biol. 264:350-63.

Tolosa, et al., (1999) Glucose Sensor for Low-Cost Lifetime-Based Sensing Using a Genetically Engineered Protein. Anal. Biochem. 267:114-20.

Rosenzweig, Z. and Kopelman R., Analytical Properties and Sensor Size Effects of a Micrometer-Sized Optical Fiber Glucose Biosensor, Anal. Chem. 1996, 68, 1408-1413.

* cited by examiner

Biosensor

Figure 1

2 = optical system
3 = computer/microprocessor
4 = optical conduit
5 = disposable tip
6 = sensing element

Tip Designs
Figure 3

FIBER OPTIC DEVICE FOR SENSING ANALYTES

This is a continuation of U.S. application Ser. No. 10/721,797, filed 26 Nov. 2003, the contents of which are incorporated herein by reference in its entirety.

FIELD OF THE INVENTION

The present invention relates to a device that can be used to monitor concentrations of physiologically relevant compounds.

BACKGROUND OF THE INVENTION

Monitoring in vivo concentrations of physiologically relevant compounds to improve diagnosis and treatment of various diseases and disorders is a desirable goal and would enhance the lives of many individuals. Advances in this area show particular promise in the area of facilitating adequate metabolic control in diabetics. Currently, most diabetics use the "finger stick" method to monitor blood glucose level, and patient compliance is problematic due to pain caused by frequent finger sticks. As a consequence, there have been efforts to develop non-invasive or minimally invasive in vivo and more efficient in vitro methods for frequent and/or continuous monitoring of glucose in the blood or other biological fluids.

The approaches to frequent and/or continuous in vivo monitoring tend to fall into two general categories: "non-invasive" and "minimally invasive." Non-invasive monitoring determines analyte levels by directly tracking spectroscopic changes in skin and tissue. Infrared radiation and radio wave impedance spectroscopy are examples of this technology. Progress with these approaches has been slow due to the requirement for frequent calibration, reproducible sample illumination, and variances in spectroscopic backgrounds between individuals. The "minimally invasive" approach avoids direct extraction of blood from the body and relies on the monitoring of signal changes in biological fluids using an intermediate sensing element. Biosensors of this type are devices capable of providing specific quantitative or semi-quantitative analytical information using a biological recognition element that is combined with a transducing (detecting) element.

Most conventional systems for frequent or continuous analyte monitoring involve amperometric biosensors that employ enzymes such as glucose oxidase (GOx) to oxidize glucose to glucuronic acid and hydrogen peroxide, generating an electrochemical signal. These sensors are subject to inaccurate measurement due to oxygen deficiency and buildup of oxidation by-products. An accurate measurement of glucose concentrations requires an excess of oxygen, which is generally not present in human blood or interstitial fluid. Also, the electrochemical reaction itself generates a buildup of oxidation byproducts that may inhibit and degrade both the enzyme and its protective layer.

Biosensors based on optical rather than electrochemical signals have also been developed and may offer significant improvements in stability and calibration. For example, referencing an analyte-dependent optical signal against a second analyte-independent signal can correct for sources of noise and instability in the sensor. However, the potential of optical sensing for in vivo analyte detection has not yet been realized. One reason for this is that many current optical sensing methods rely on enzymatic chemistry such as glucose oxidase. In one common method, an oxygen-sensitive fluorescent dye is used to monitor the consumption of oxygen by the GOx enzymatic reaction. Although this is an optical biosensor, with the fluorescence signal level varying with changing oxygen levels, such a sensor is subject to the same problems as amperometric devices based on this same chemistry: oxygen deficiency and enzyme degradation.

To overcome the challenges associated with enzyme sensing (e.g., GOx), whether electrochemical or optical, non-enzymatic protein-based optical or fluorescent sensing is being explored. Labeled concanavalin A and dextran have been used to create a competitive FRET assay; however, this system requires entrapment of both components, and the dynamic range of the assay is limited. See Ballerstadt, R., Schultz, J. S.; "Competitive-binding assay method based on fluorescence quenching of ligands held in close proximity by a multivalent receptor." Anal. Chem. Acta 345 (1-3): 203-212 (1997). See also, Russell, R. J., Pishko M. V., Gefrides C. C., McShane, M. J., Cote, G. L.; "A fluorescence-based glucose biosensor using concanavalin A and dextran encapsulated in a poly(ethylene glycol) hydrogel" Anal. Chem. 71 (15): 3126-3132 (1999).

Another protein-based sensing chemistry uses the *Escherichia coli* (*E. coli*) periplasmic receptor, glucose-galactose binding protein (GGBP) to generate a fluorescence signal in response to glucose binding. See, for example, Tolosa, L., I. Gryczynski, L. R. Eichhorn, J. D. Dattelbaum, F. N. Castellano, G. Rao, and J. R. Lakowicz; "Glucose sensor for low-cost lifetime-based sensing using a genetically engineered protein" Anal. Biochem. 267:114-120 (1999); Helling a, H. W., and J. S. Marvin; "Protein engineering and the development of generic biosensors. Trends Biotechnol" 16:183-189 (1998); Salins, L. L., R. A. Ware, C. M. Ensor, and S. Daunert; "A novel reagentless sensing system for measuring glucose based on the galactose/glucose-binding protein" Anal Biochem 294:19-26 (2001); and de Lorimier, R. M., J. J. Smith, M. A. Dwyer, L. L. Looger, K. M. Sali, C. D. Paavola, S. S. Rizk, S. Sadigov, D. W. Conrad, L. Loew, and H. W. Hellinga. "Construction of a fluorescent biosensor family" Protein Sci. 11:2655-2675 (2002). GGBP undergoes a substantial conformation change upon ligand binding, trapping the ligand between its two globular domains. See, for example, Shilton, B. H., M. M. Flocco, M. Nilsson, and S. L. Mowbray; "Conformational changes of three periplasmic receptors for bacterial chemotaxis and transport: the maltose-, glucose/galactose- and ribose-binding proteins" J. Mol. Biol. 264:350-363 (1996). By site-specifically labeling the protein with an environmentally sensitive fluorophore this attribute can be exploited to generate a fluorescent signal. See, for example, Salins, L. L., R. A. Ware, C. M. Ensor, and S. Daunert; "A novel reagentless sensing system for measuring glucose based on the galactose/glucose-binding protein" Anal Biochem 294:19-26 (2001). Because GGBP neither consumes glucose nor generates reaction products, it can be used as a reagentless sensor. This may provide greater accuracy and reliability than amperometric biosensors.

While a number of groups have developed GGBP mutations capable of responding to glucose in the physiological range, there have been no reports of a functional biosensor device based on binding protein technology that is suitable for in vivo analyte monitoring. A functional frequent and/or continuous biosensor must couple the sensing element to the optical sensing elements while maintaining sensor integrity and functionality as well as patient comfort. For example, the biological recognition element and accompanying transducing element should preferably be incorporated within biocompatible material that shields the sensing element from the immune system, permits analyte diffusion in and out, and avoids leaching of the sensing element into the patient blood or other biological fluid (e.g., interstitial fluid). Since binding proteins require orientational control and conformational freedom to enable effective use, many physical absorption and random or bulk covalent surface attachment or immobilization strategies as taught in the literature generally are either suboptimal or unsuccessful. Further, a means for interrogating the sample with light in a reproducible and/or controlled fashion must be devised.

One approach generally known is to couple the sensing element to one end of an optical fiber and to couple the optical elements such as excitation sources or detectors to the other end. However, coupling of binding proteins to one end of an optical fiber is subject to the above-mentioned challenge of preserving conformational and/or orientational mobility of the protein. In addition, fiber optic cabling is often impractical from a patient-use point of view since patients may need to remove or replace the sensor periodically. Replacement of the entire fiber can be costly and inconvenient. Finally, the optical system, comprising, e.g., excitation sources, detectors, and other optical elements must be sufficiently robust to tolerate or correct for changes in optical alignment due, for example, to patient motion or drift of the electronics in the optical reader. The optical system must also be sufficiently sensitive to detect signal from reporter dyes without relying on high power consumption and/or large-sized elements that would render the system unportable and hence unwearable.

Accordingly, there is a need for a biosensor that incorporates in its sensing element a binding protein with conformational and/or orientational mobility coupled to optical sensing elements that provide a wearable and robust device.

SUMMARY OF THE INVENTION

An object of the present invention is to provide a device for sensing the concentration of a target analyte in a sample. The sample may be blood, saliva, tears, sweat, urine, cerebral spinal fluid, lymph fluid, interstitial fluid, plasma, serum, animal tissue and media. The device comprises: (i) an optical conduit having a proximal end and a distal end; (ii) an optical system at the proximal end of the optical conduit that contains at least one electromagnetic energy emitter and at least one electromagnetic energy detector; and (iii) a sensing element in optical proximity to the distal end of the optical conduit that comprises at least one binding protein that is adapted to bind with at least one target analyte; said sensing element also comprising at least one reporter group, and optionally one or more reference groups.

The optical conduit, which may vary in length from approximately 0.1 cm to 1 meter, couples light into and out of the optical system and into and out of the sensing element. For example, the optical conduit may be a lens, a reflective channel, a needle, or an optical fiber. The optical fiber may be either a single strand of optical fiber (single or multimode) or a bundle of more than one fiber. In one embodiment, the bundle of fibers is bifurcated. The fiber may be non-tapered or tapered so that it can penetrate the skin of a patient.

The optical system consists of a combination of one or more excitation sources and one or more detectors. It may also consist of filters, dichroic elements, a power supply, and electronics for signal detection and modulation. The optical system may optionally include a microprocessor.

The optical system interrogates the sample either continuously or intermittently by coupling one or more interrogating wavelengths of light into the optical conduit. The one or more interrogating wavelengths then pass through the optical conduit and illuminate the sensing element. A change in analyte concentration results in a change of the wavelength, intensity, lifetime, energy transfer efficiency, and/or polarization of the luminescence of the reporter group, which is a part of the sensing element. The resulting changed luminescence signal passes back through the optical conduit to the optical system where it is detected, interpreted, and stored and/or displayed. In certain embodiments, the optical system comprises multiple excitation sources. One or more of these sources may be modulated to permit dynamic signal processing of the detected signal, thereby enhancing signal-to-noise and detection sensitivity. Modulation may also be used to reduce power consumption by the device or to increase the lifetime of the sensing element by minimizing undesirable phenomena such as photobleaching. The optical system can also include one or more electromagnetic energy detectors that can be used for detecting the luminescence signal from the reporter and optional reference groups as well as for internal referencing and/or calibration. The overall power consumption of the optical system is kept small to permit the device to be operated using battery power.

The sensing element comprises one or more binding proteins that are adapted to bind with at least one target analyte, and at least one reporter group. A suitable binding protein may be any that is adapted for use as a biosensor. For example, the suitable binding protein may be any one of those described in copending, commonly owned U.S. patent application Ser. No. 10/039,833 filed Jan. 4, 2002; U.S. patent application Ser. No. 10/040,077 filed Jan. 4, 2002; U.S. patent application Ser. No. 10/039,799 filed Jan. 4, 2002; and U.S. Patent Application for "Compositions and Methods for Measuring Analyte Concentrations" to Terry Amiss, et al. (attorney docket no. P-6011) filed on even date herewith, the contents of which are incorporated herein by reference in their entirety. Suitable binding proteins may also be any one of those described in U.S. Pat. Nos. 6,277,627, 6,197,534, or WO 03/060464 A2 the entire contents of which are incorporated herein by reference in their entirety.

The reporter group, which is associated with the binding protein, is adapted to undergo a luminescence change upon binding of the binding protein to the target analyte. As used herein, the term "associated with" means that the reporter group is covalently or non-covalently associated with the binding protein such that upon binding of a target analyte to the binding protein, there is a change in the reporter group's luminescence properties such as wavelength, intensity, lifetime, energy transfer efficiency, and/or polarization. Examples of reporter groups include, but are not limited to, organic dyes, pairs of organic dyes, fluorescent or bioluminescent fusion proteins, pairs of fluorescent or bioluminescent fusion proteins, or any combination of the above. The reporter group may consist of a donor and acceptor undergoing fluorescence resonance energy transfer. Other luminescent labeling moieties include lanthanides such as europium ($Eu^{3+}$) and terbium ($Tb^{3+}$), as well as metal-ligand complexes, including those of ruthenium [Ru (II)], rhenium [Re (I)], or osmium [Os (II)], typically in complexes with diamine ligands such as phenanthrolines.

The sensing element is in optical proximity to the optical conduit. "Optical proximity" means that components of the device are close enough to one another such that an optical signal can be transmitted to or received from one object by another. The sensing element may be placed in optical proximity to the optical conduit in a number of ways, for example: attached directly to the optical conduit; attached to a connector that is attached to the optical conduit; attached to a polymer chain or a polymer matrix that is attached to the optical conduit; or attached to a polymer chain or a polymer matrix that is attached to a connector that is attached to the optical conduit. The sensing element may be permanently affixed to the optical conduit or replaceably attached such that the sensing element can be replaced conveniently and economically.

In another embodiment, the sensing element may further comprise one or more reference groups. Unlike the reporter group, the reference group has a luminescence signal that is substantially unchanged upon binding of the target analyte to the binding protein. "Substantially unchanged" means the luminescence change of the reference group is significantly less than the luminescence change undergone by the reporter group. The reference group, which can consist of luminescent dyes and/or proteins, is used for internal referencing and calibration. The reference group can be attached to any number of components of the device including the sensing element, a binding protein not containing the reporter group, the polymer matrix, the polymer chain, a biomolecule that is not a binding protein, the optical conduit, or a tip.

The sensing element (typically this refers to the binding protein with the associated reporter group and optional reference group) may be attached directly to the distal end of the optical conduit using for example covalent, ionic, or van der Waals interactions, dip coating, spin coating, plasma coating, or vacuum deposition. The sensing element may also be attached to a connector, which allows the sensing element to be readily detachable so that it becomes replaceable.

In another embodiment, the sensing element is attached to or immobilized in a polymeric matrix. The polymer matrix may be any matrix that permits free diffusion of the analyte of interest into and out of the matrix, while excluding interfering immune proteins and proteases and allows the binding protein to retain some degree of conformational and/or orientational mobility. The matrix may consist of multiple layers, with an inner layer serving to retain the binding protein, and one or more outer layers to control the permeability and/or achieve biocompatibility. For example, the polymer matrix may be any one of those described in copending, commonly owned U.S. application Ser. No. 10/428,295, filed May 2, 2003, the entire contents of which are incorporated herein by reference. The immobilization may be accomplished either by covalently linking the sensing element to the polymer matrix or by physically entrapping the sensing element within the matrix. In the instance where the polymer matrix physically entraps the sensing element, the matrix pores are sized to retain the sensing element. In the embodiment where the sensing element is attached to the polymeric matrix, the sensing element is attached to the matrix using, for example, covalent or ionic linkage. The polymer matrix can be attached to the distal end of the optical conduit using adhesives, dip or spin coating, plasma coating, covalent, ionic, or van der Waals interactions, a mechanical connector or combinations thereof.

In another embodiment, the sensing element is attached to a polymeric chain. The method of attaching the sensing element to the polymeric chain includes, but is not limited to, covalent, ionic, and van der Waals interactions and combinations thereof. The polymer chain is attached to the distal end of the optical conduit using, for example, dip or spin coating, plasma coating, vacuum deposition, covalent, ionic, or van der Waals interactions, or combinations thereof.

In another embodiment, the device further comprises a tip (either tapered or non-tapered) that is designed to pierce the skin to allow the sensing element to contact body fluids. Preferably, the tip is disposable. The tip may be made of plastic, steel, glass, polymer, or any combination of these or similar materials. The tip may be attached directly to the optical conduit (fiber) using adhesives or a mechanical fitting. The tip may also be used to house the optical conduit containing the sensing element, such that it encases the optical conduit and sensing element. In one embodiment, the sensing element may be contained within the tip.

The device may further comprise a connector that may be used to attach the components of the device to one another. The connector may be, for example, any mechanical device, such as standard fiber optic connectors, luer locks, plastic, metal, or glass sleeves, or spring-loaded housings. For instance, the connector may be used to attach the sensing element to the optical conduit, or to attach the optical conduit to the optical system. The primary purpose of the connector is to provide a component that allows the other components to be readily detachable so that the component becomes replaceable.

In light of the foregoing comments, it will be recognized that a principal object of the present invention is to provide an improved device for sensing the concentration of a target analyte that is wearable and easy to operate. Preferably, the device may be used for continuous analyte monitoring, but someone skilled in the art could envision continuous and episodic monitoring of in vivo and/or in vitro samples with such a device.

Another object of the present invention is to provide a device that is compact in design and portable.

A further object of the present invention is to provide a device for sensing a target analyte that is robust.

A further object of the present invention is to provide a device that can be easily employed with highly reliable results.

Another object of the present invention is to provide a device that is accurate and provides readings in a short time span.

Another object of the present invention is to provide a device that has a tip portion of a size so that it produces little or no pain or sensation when inserted into a patient.

These and other objects and advantages of the present invention will become apparent after considering the following detailed specification in conjunction with the accompanying drawings.

BRIEF DESCRIPTION OF THE DRAWINGS

The invention will be more readily understood with reference to the embodiments thereof illustrated in the attached drawing figures, in which.

Throughout the drawing figures, it should be understood that like numerals refer to like features and structures.

DETAILED DESCRIPTION OF THE PREFERRED EMBODIMENTS

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The present invention involves a binding-protein engineered to bind an analyte of interest within a desired clinical or analytical range. In addition, one or more luminescent reporter groups are associated with the binding protein. These luminescent reporter groups include but are not limited to, for example, organic aromatic dye molecules covalently coupled to cysteine residues in the protein or, for example, luminescent biomolecules such as proteins fused to the engineered binding protein. Cysteine or other amino acid groups may be engineered into the binding protein to provide sites of attachment for the luminescent reporter molecule. Binding of the analyte to the binding protein results in a change in the luminescent properties of one or more reporter groups. The luminescent property affected may be the absorption or emission wavelength, absorption or emission intensity, emission lifetime, emission polarization, and/or energy transfer efficiency. Binding of the analyte is also reversible, with the unbinding resulting again in a change in the luminescent properties of the reporter molecule.

The one or more binding proteins along with their associated reporter groups comprise the sensing element. Optionally, the sensing element may also contain one or more reference groups. Unlike the reporter group, the reference group has a luminescence signal that is substantially unchanged upon binding of the target analyte to the binding protein. The luminescence signal from the reference group provides an internal optical standard that can be used to correct for optical artifacts due to for example electronic drift in the optical system or to motion of the sample or optical conduit. The reference group can also be used for calibration. The reference group can be attached to any number of components of the device including the sensing element, a binding protein not containing the reporter group, the polymer matrix, the polymer chain, a biomolecule that is not a binding protein, the optical conduit, or the tip. In one embodiment, the reference group is attached to a binding protein that has been engineered to show no significant response to the analyte at physiologically relevant concentrations.

The sensing element, comprising one or more binding proteins, one or more reporter groups, and optional reference groups, may be immobilized at the end of the optical conduit or inside a disposable tip that interfaces with the optical conduit. Immobilization of the sensing element on the optical conduit or inside the disposable tip may be accomplished by depositing a thin layer of the sensing element, for example, by dip or spin coating, covalent attachment, plasma treatment, and the like directly onto the optical conduit or tip. Alternately, the sensing element can be first immobilized in a polymeric matrix and the matrix then attached to the optical conduit, or tip either by adhesives, injection molding, dip or spin coating, plasma coating, vacuum deposition, ink jet technology, covalent, ionic, or van der Waals interactions, by mechanical attachment or any combination thereof.

The optical system is capable of interrogating the luminescent response of the reporter and reference groups by passing light from an electromagnetic excitation source down the optical conduit to the distal end containing the sensing element. The optical system also monitors and interprets the return signals generated by the luminescence response of the reporter group and reference group. The luminescent properties of the reporter group, either wavelength, intensity, lifetime, energy transfer efficiency, or polarization, change in response to analyte binding or unbinding from the binding protein.

Figure 1:
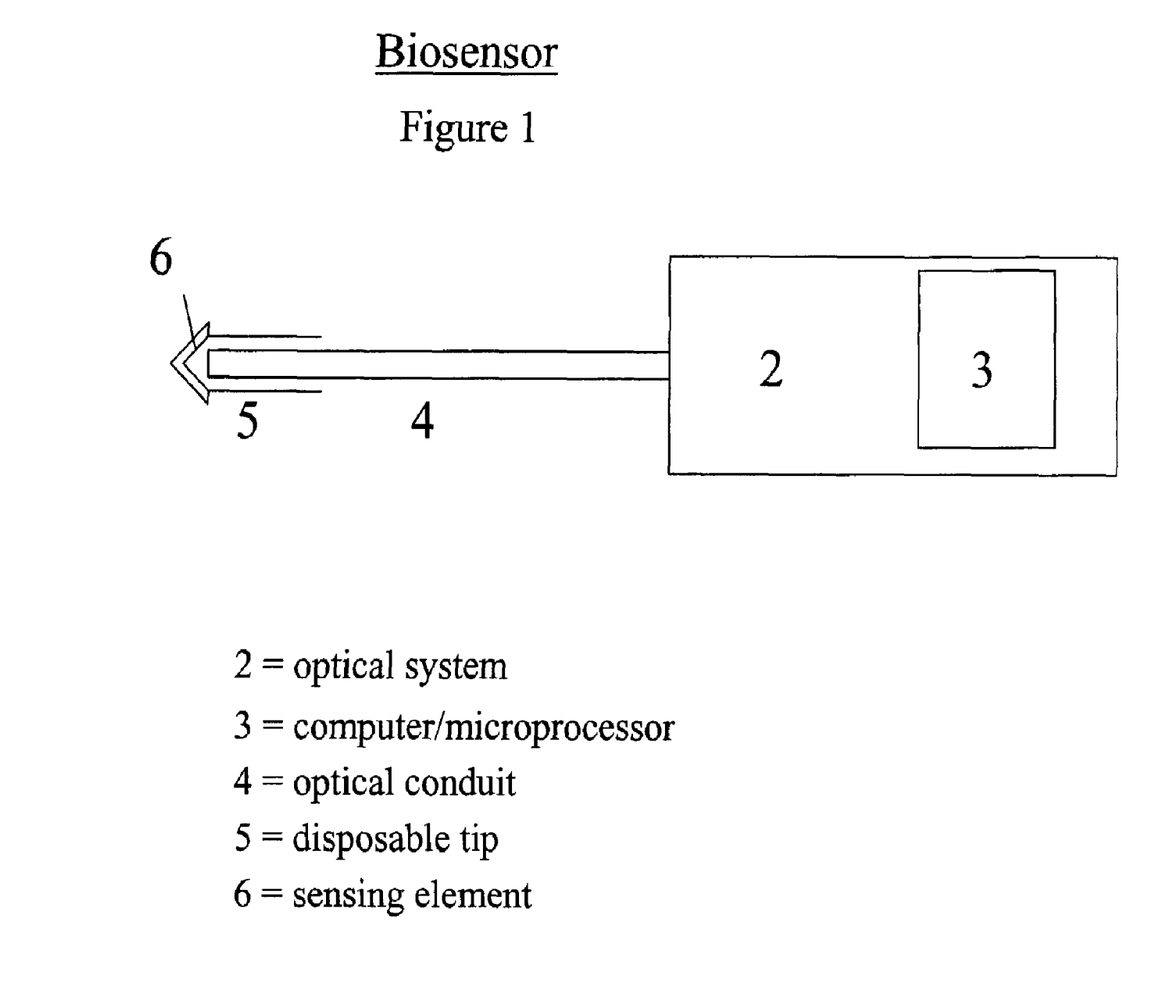
FIG. 1 is a generalized schematic of a biosensor according to an embodiment of the invention.

Now with reference to FIG. 1 a specific exemplary embodiment of the present invention will be described. The optical system 2 includes a combination of elements including but not limited to electromagnetic energy emitters, electromagnetic energy detectors, various mirrors, filters, electronics, holographic optics, dichroic elements, and optical standards needed to send interrogating radiation from the electromagnetic energy emitter down the optical conduit to the sensing element and then to resolve and interpret the return luminescent signal. The return luminescent signal from the reporter group changes in response to changing concentrations of the analyte to be detected. The optical system 2 may also comprise a computer or microprocessor 3 which handles signal processing, mathematical manipulation of one or more signals, and data storage and handling. The computer or microprocessor 3 may be in physical contact with the other components of the optical system or, in a preferred embodiment, may be physically separated by up to several meters from the other components of the optical system. In this embodiment, information from the electromagnetic energy detectors and electronic processing elements in the optical system is communicated wirelessly to the computer or microprocessor 3. The computer or microprocessor 3 may also store calibration information specific to the sensing element. Light of one or more wavelengths produced in the optical system 2 is channeled down an optical conduit 4 to the sensing element 6. Optical conduit 4 may be either an optical fiber or a short light guide that transmits light with minimal loss. The sensing element 6 consists of one or more binding proteins with one or more associated luminescent reporter groups either immobilized in a polymeric matrix, attached to a polymer chain, incorporated in a disposable tip, attached directly to the distal end of the optical conduit, or attached to a connector. The sensing element 6 can also consist of additional luminescent reference groups that are optionally attached to biomolecules, polymers, or organic molecules for the purpose of providing a reference or calibration signal. Sensing element 6 can be attached to the distal end of optical conduit 4, either directly or via a polymer matrix, or, in the preferred embodiment, attached to a disposable tip 5 that is attached to the distal end of the optical conduit 4. In this case, the disposable tip 5 is positioned against optical conduit 4 either mechanically, via adhesive, or by any other suitable means known to those of skill in the art.

Figure 2:
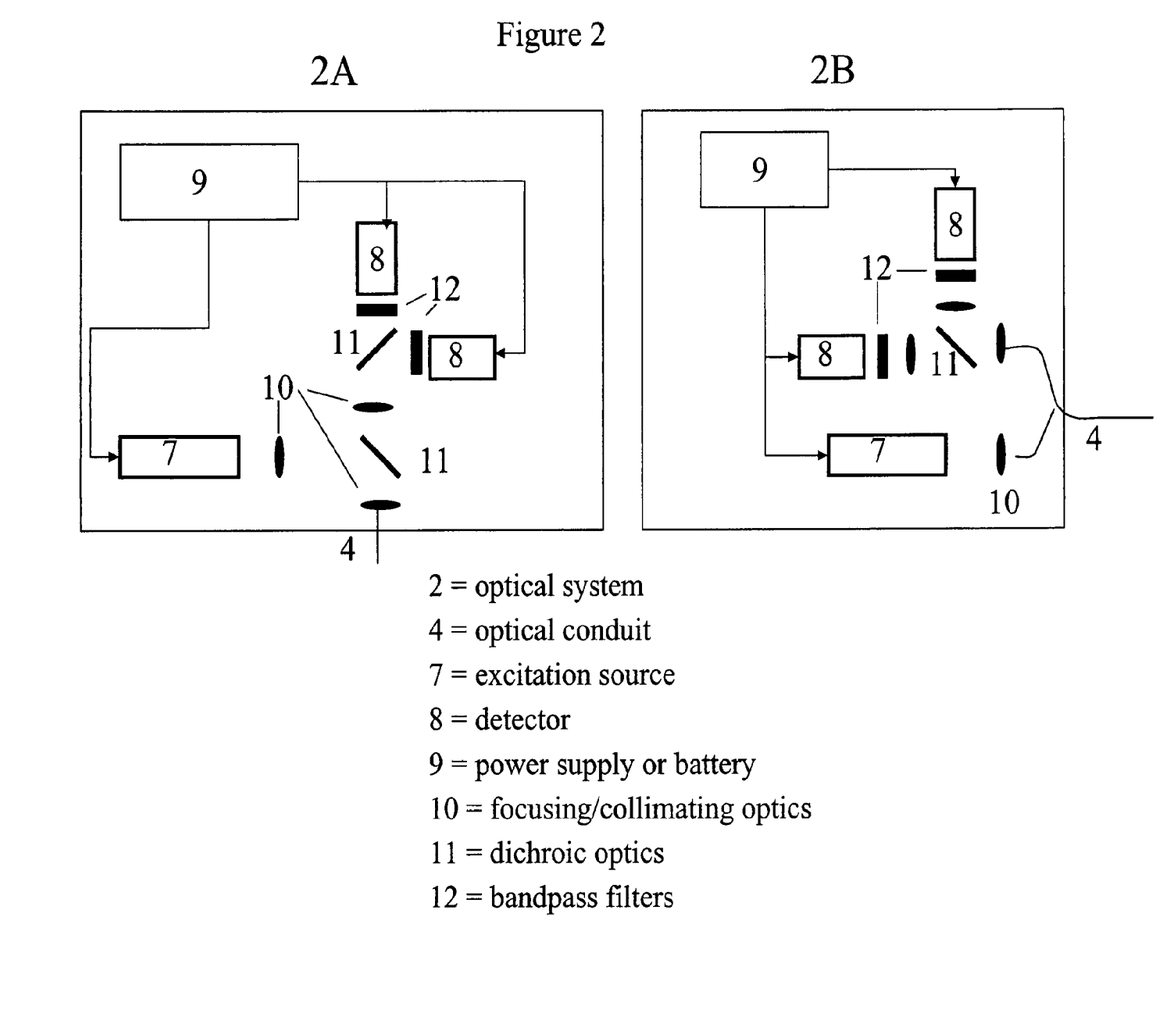
FIG. 2 illustrates two embodiments of the optical configuration in the optical portion of the sensor according to an embodiment of the present invention.

FIG. 2 is an enlargement of the optical system 2 in two typical embodiments. In FIG. 2A, a dichroic mirror or beamsplitter 11 is used to direct light from an electromagnetic energy source 7 to the optical conduit 4. Excitation sources may consist of, but are not limited to, for example arc lamps, laser diodes, or LEDs. In this embodiment, the optical conduit 4 is a fiber optic cable, and the same fiber is used to transmit excitation light from electromagnetic energy source 7 to the sensing element 6 and also to transmit the luminescence signals from the reporter or reference groups back to the optical system 2. A dichroic element 11 preferably separates the return signal from the excitation light and directs the signal to electromagnetic energy detectors 8. Detectors may consist of, but are not limited to, for example, photodiodes, CCD chips, or photomultiplier tubes. In the event that multiple luminescent signals are returned from the sensing element, additional dichroic elements may be used to direct portions of the return signals to multiple detectors. Preferably, a luminescent reference group that is analyte insensitive is included along with the analyte-dependent reporter molecule to provide a reference signal. This reference signal can be used, for example, to correct for optical or electronic drift.

FIG. 2B illustrates a second embodiment in which a bifurcated optical bundle or fused optical fiber arrangement is used to transmit light to and from the sensing element. Here, light from excitation source 7 is transmitted down one arm of the bifurcated fiber bundle. Return luminescent signals from the sensing element are detected using the second arm of the bifurcated fiber, so that in this case the fiber bundling serves to separate excitation from return luminescence. Dichroic optics, beamsplitters, or polarizers may additionally be used to further divide the return luminescence, based for example on wavelength or polarization. Optionally, bandpass filters 12 can be used to select the luminescent wavelength to be detected. Power supply 9 supplies power to the optical system 2.

Figure 3:
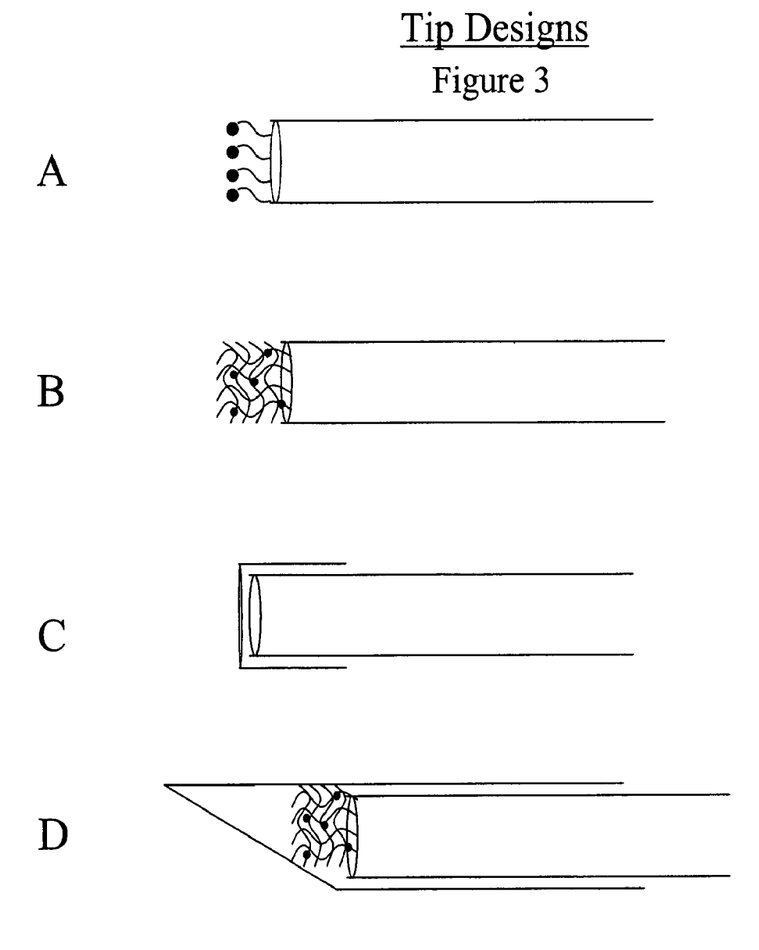
FIG. 3 illustrates various embodiments of the biosensor tip according to an embodiment of the invention.

FIG. 3 illustrates representative methods of attaching the sensing element to the end of an optical conduit, when the optical conduit is an optical fiber. In FIG. 3A, the sensing element attached directly to the distal end of the optical fiber using for example covalent, ionic, or van der Waals interactions, dip coating, spin coating, plasma coating, vacuum deposition, ink jet technology, or combinations thereof. Alternately, the sensing element, comprising the binding proteins, associated reporter groups, and optional reference groups, can be attached to a long chain polymer, and the long chain polymer attached directly to the distal end of the optical fiber using for example, dip or spin coating, plasma coating, vacuum deposition, covalent, ionic, or van der Waals interactions, ink jet technology, or combinations thereof.

In FIG. 3B, the sensing element is immobilized in a polymeric matrix and the polymer matrix is attached to the distal end of the optical fiber using, for example, adhesives, dip or spin coating, plasma coating, injection molding, ink jet technology, covalent, ionic, or van der Waals interactions, a mechanical connector or combinations thereof. In a preferred embodiment, reactive groups of the polymer matrix and/or protein are used to covalently bond the sensing element directly to the optical fiber, such as for example by introducing amine groups on the surface of a glass or silica fiber. In FIG. 3C, a plastic or polymer sleeve fits over the distal end of the optical fiber and serves to house and protect the sensing element. The sensing element is entrapped in or attached to a polymer matrix. The polymer matrix containing the sensing element can be introduced into the sleeve either by injection, pouring, or dipping and can then be cross-linked or polymerized within the sleeve. Alternatively, the sensing element may be polymerized within the sleeve prior to insertion of the fiber optic. FIG. 3D shows the optical fiber held within the inside of the needle. The needle may have a modified bevel to control piercing depth and/or a side port to permit access of the analyte to the sensing element contained in the needle. The sensing element inside the needle may be attached directly to the optical fiber using any of the methods described in the discussion of FIG. 3A, 3B, or 3C or, alternatively, may have only mechanical contact with the fiber. The attachment schemes shown in FIG. 3 are preferred embodiments and may be used either individually or in combination.

Figure 4:
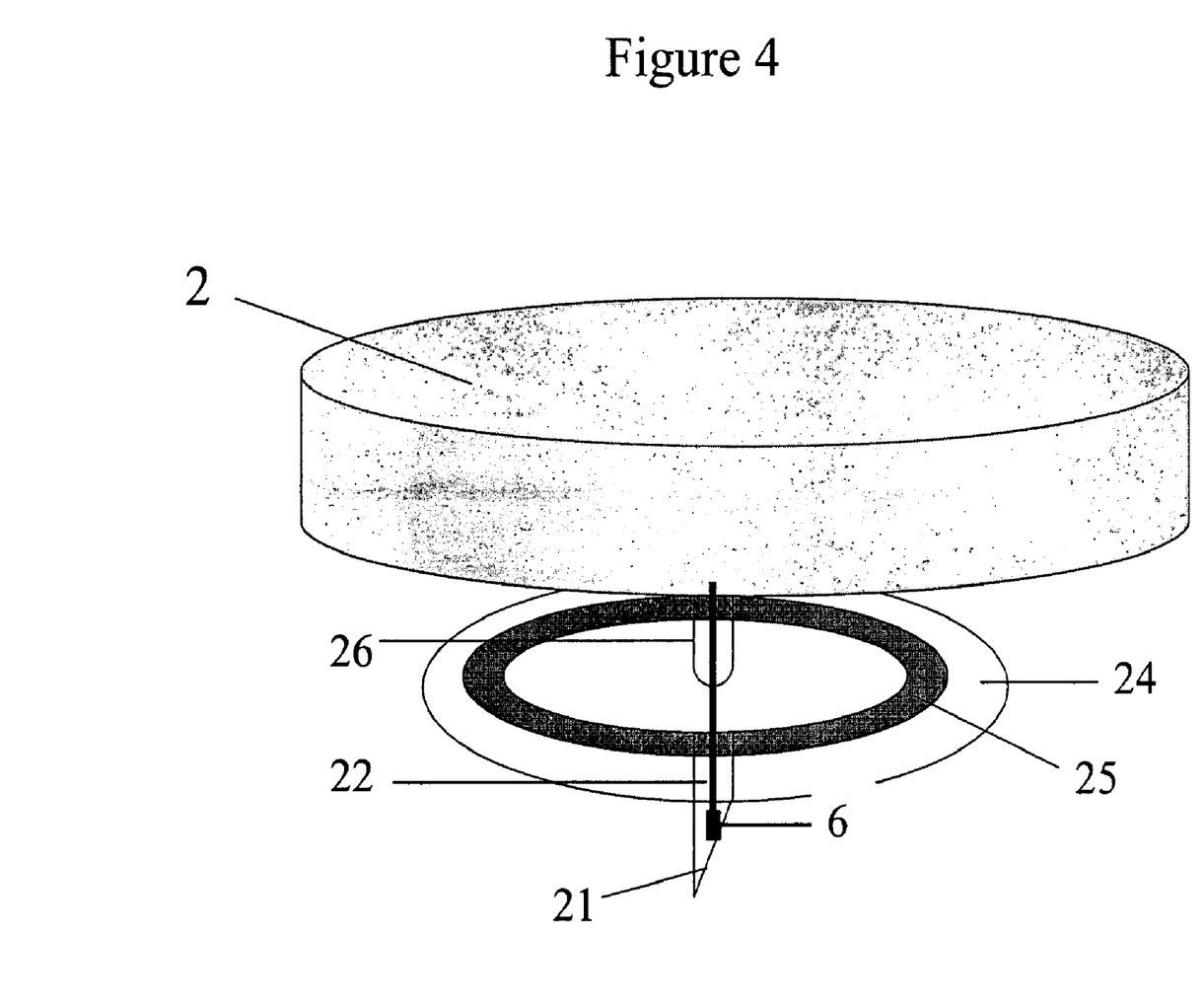
FIG. 4 illustrates an embodiment of the invention that is a wearable in-vivo optical biosensor.

FIG. 4 shows a preferred embodiment of a wearable optical biosensor. The tip, 21, is a steel needle approximately 1-10 mm in length, containing within it the sensing element, 6, immobilized onto an optical fiber, 22. The fiber, tip, and needle assembly is centered in a plastic mount, 24. The tip, containing the optical fiber and the sensing element, is inserted perpendicularly into the skin of a patient so that the chemistry at the end of the fiber resides in either the intradermal or subcutaneous space. Adhesive ring 25 then holds the plastic mount plus needle assembly in place. The optical system 2, then clamps over the plastic assembly, with the connector 26 interfacing the optical fiber 22 with the optical system. The optical system can be designed, for example, according to either optical embodiment 2a or 2b. Excitation sources may consist of, but are not limited to, for example arc lamps, laser diodes, or LEDs. Detectors may consist of, but are not limited to, for example, photodiodes, CCD chips, or photomultiplier tubes.

The following examples illustrate certain preferred embodiments of the instant invention, and are merely intended to be illustrative of exemplary embodiments. Labeled mutated binding proteins with fluorophore reporter probes are used herein in accordance with the procedure set forth by Cass et al., *Anal. Chem.* 1994, 66, 3840-3847, or as otherwise described.

EXAMPLE 1

According to one embodiment of the present invention, glucose galactose binding protein (GGBP) was used with a triple mutation including a cysteine substituted for an glutamic acid at position 149, an arginine substituted for an alanine at position 213 and a serine substituted for leucine at position 238 (E149C/A213R/L238S). The protein was labeled at the 149 position with N,N'-dimethyl-N-(iodoacetyl)-N'-(7-nitrobenz-2-oxa-1,3-diazol-4-yl)ethylenediamine (IANBD amide)oxy. This mutated GGBP (E149C/A213R/L238S) is specific for glucose, and the reporter group undergoes a fluorescence intensity change in response to glucose binding.

A multicoated or multilayer matrix was prepared as follows. A core matrix was formed by mixing 1 part dye-labeled binding protein (15 uM in PBS buffer, pH 7.4, prepared as described in PCT/US03/00203) with 2 to 4 parts 3 wt % alginate (v/v) in a scintillation vial and vortexing at slow speed. 3 mL of the resulting protein-alginate mixture was placed in a syringe and infused at a rate of 10 mL/hr into 200 ml of 1 M $CaCl_2$ on a mixer, thereby forming beads of about 0.4 to 1.5 mm in diameter. The beads were mixed in $CaCl_2$ solution on the mixer for 15-60 minutes. A containment layer was then formed by placing the beads from above in a solution of poly-L-lysine 0.01% w/v in water, approximately 10 mL, for 1 hour, then drying the poly-lysine coated beads on an absorbent towel for 15 to 30 minutes. At this point the sensor was ready to be used.

The fiber used in this embodiment was a bifurcated fiber optic. It contained six 400 um fibers arranged around a central 400 um fiber. The six fibers were used as the excitation conduit and the central fiber as the detection conduit. The total diameter of the fiber was 1.4 mm. Once the fiber was polished, Loctite 4011 medical grade glue was used to adhere the sensing element to the distal end of the fiber optic. The proximal end of the fiber was bifurcated, with one arm going to an excitation source and the other arm going to a detector. A 470 nm LED was used as the excitation source, and a commercial fluorescence spectrometer was used as the electromagnetic energy detector. The emission intensity at 540 nm was then measured.

Figure 5:
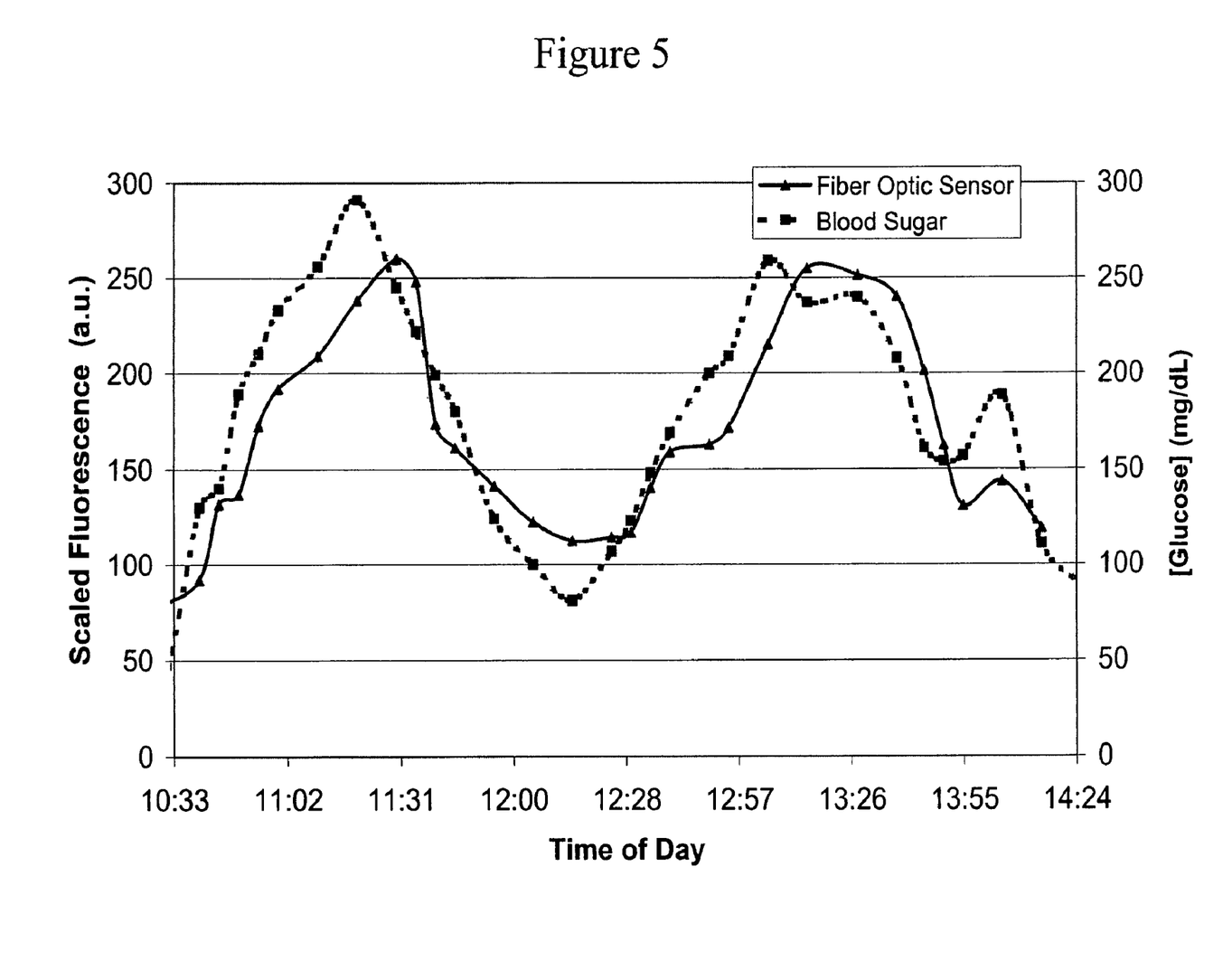
FIG. 5 is a chart showing the performance of a fiber optic biosensor according to an embodiment of the invention tracking changing glucose levels in an anesthetized pig.

In a trial, the distal end and sensing element of a biosensor formed in this manner was inserted through a 13 gauge needle into the side of an anesthetized pig, approximately 1-2 mm under the skin. Alternating solutions of lactated ringer's with and without 10% dextrose were infused through the ear vein of the pig to increase and decrease the pig's glucose levels in a controllable fashion. At intervals, blood samples were pulled from the vena cava of the pig through a throat catheter, and blood sugar readings were tested on a handheld blood glucose meter. The fluorescence intensity of the biosensor was observed to track changing glucose levels in the anesthetized pig, as shown in FIG. 5.

EXAMPLE 2

In another embodiment, the binding protein was glucose galactose binding protein (GGBP), with a cysteine substituted for an glutamic acid at position 149, an arginine substituted for an alanine at position 213 and a serine substituted for leucine at position 238 (E149C/A213R/L238S). The protein was labeled at the 149 position with N,N'-dimethyl-N-(iodoacetyl)-N'-(7-nitrobenz-2-oxa-1,3-diazol-4-yl)ethylenediamine (IANBD amide). The biosensor was prepared by inserting the tip of a 400 micron core diameter fiber into a short piece of catheter tubing, and allowing the catheter tubing to overhang the fiber tip by 0.1-1 mm. The fiber comprised a silica core, silica cladding, and polyimide buffer. The fiber diameter was 400/440/470 microns, where the slashes denote diameters measured from the core/cladding/buffer exteriors.

The immobilization matrix was a crosslinked alginate-based hydrogel, prepared by covalently crosslinking Pronova™ UP LVG alginate through the carboxyls with adipic acid dihydrazide (AAD) via carbodiimide chemistry. Pronova™ UP LVG was selected in this embodiment for its low viscosity and high guluronic to mannuronic ratio. A 2% alginate solution was prepared by dissolving 1 gram of alginate in 50 mL 0.1 M MES buffer (pH 6.5) and then adding 110 mg of AAD and 79 mg of hydroxybenzotriazole (HOBt). The solution was stored at 4° C. until used. To the alginate solution, 145 mg of 1-ethyl-3-(3-dimethylamino-propyl) carbodiimide (EDC) was added per 10 mL of solution, using a dual-syringe mixing technique. The alginate, AAD, HOBt, EDC mixture was aspirated into a 1 mL syringe, and a blunt 30 gauge needle was attached to the syringe. The needle was primed, and then the tip was inserted into the catheter tubing mold on the optical fiber. The catheter tubing on the fiber was filled, ensuring good contact between the tip of the fiber optic and the alginate matrix. The matrix was allowed to cross-link for 15 minutes, and then the fiber tip and matrix assembly were transferred to a 0.1M, 6.5 pH MES solution, where they were stored for 2 hours. At the end of the two hours, the sensing tips were placed in excess phosphate buffer solution (PBS, 0.0027 M potassium chloride, 0.137 sodium chloride, pH 7.4 where they were stored a minimum of 30 minutes to quench the reaction.

To attach binding protein, the tips were incubated in a solution of labeled GGBP in PBS buffer [NBD-E149C/A213R/L238S GGBP] (53 uM, 50 uL) for approximately 8 hours. The sensors were protected from ambient light during incubation. After 8-24 hours of incubation, 50 uL of EDC/NHS (200 mM/50 mM) was then added to the incubation tube. After 40 minutes, the sensor tips were removed and placed in 50 uL of 1M, pH 8.5 ethanolamine to quench the reaction. After 20 minutes in the ethanolamine solution, the sensor tips were transferred to PBS solution, where they were allowed to sit for at least 24 hours while unreacted protein diffused out. The sensors were then transferred to fresh PBS and stored in the dark until ready to use.

Figure 6:
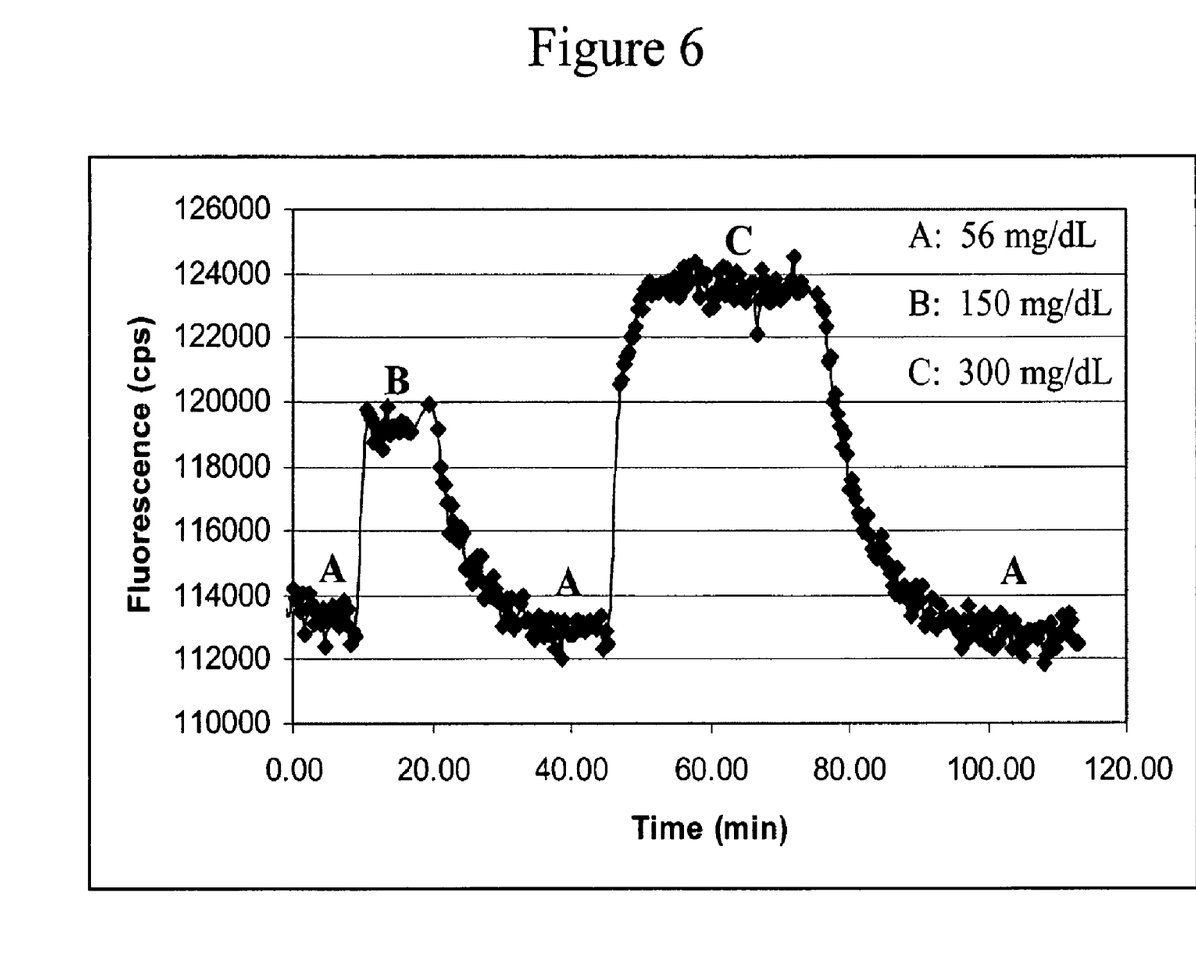
FIG. 6 is a chart showing the performance of a fiber optic biosensor according to an embodiment of the invention using a single 400 micron core fiber optic sensor and the optical configuration illustrated in FIG. 2A.

The fiber in this example was a single, 400 um core multimode fiber (silica core, silica cladding, polyimide buffer). Since in this embodiment the same fiber transmits both the excitation and luminescence signal, dichroic optics were used to separate the luminescence from the excitation, as shown in FIG. 2A. Excitation was with a 470 nm LED. A commercial dichroic filter was used to reflect the 470 nm excitation towards the input end of the fiber and transmit the fluorescence, centered at 550 nm, to the detector. Glass aspheric lenses were used both for beam collimation and to focus light into the fibers and onto the detectors. Scattered excitation was further removed from the detector using a 550 nm bandpass filter. SMA connectors permitted rapid connection and disconnection of the fiber optic sensors. The electromagnetic energy detector of this embodiment was a single photon counting photomultiplier tube. Data acquisition was performed on a laptop computer communicating with the detector through an RS-232 connection FIG. 6: In a trial, the distal end and sensing element of a biosensor formed in this manner was inserted into solutions of porcine serum containing different glucose concentrations. All porcine serum solutions were filtered through a 200 micron filter, and glucose levels in the solutions were measured on a clinical analyzer. FIG. 6 illustrates the in vitro performance of the sensor. The initial glucose level in the serum was measured to be 56 mg/dL. Serum samples at 150 and 300 mg/dL were prepared by spiking concentrated 1M glucose in PBS into serum aliquots.

EXAMPLE 3

In another embodiment of the present invention, a biosensor was formed by covalent attachment of a thin film to the surface of an optical fiber. The binding protein was glucose galactose binding protein (GGBP), with a cysteine substituted for a glutamic acid at position 149, an arginine substituted for an alanine at position 213 and a serine substituted for leucine at position 238 (E149C/A213R/L238S). The protein was labeled at the 149 position with N,N'-dimethyl-N-(iodoacetyl)-N'-(7-nitrobenz-2-oxa-1,3-diazol-4-yl)ethylenediamine (IANBD amide).

The biosensor was prepared by covalent attachment of an alginate matrix to the amine-functionalized surface of a silica fiber. The fiber comprised a silica core, silica cladding, and polyimide buffer. The fiber diameter was 400/440/470 microns, where the slashes denote diameters measured from the core/cladding/buffer exteriors.

The polyimide buffer was removed from the tip of the optical fiber by exposing the last few millimeters of the fiber to a torch for approximately 1-2 seconds. The residual polyimide was then wiped away. The tip with the buffer removed was then placed in 1 M sulfuric acid for 1 hour. Tips were then rinsed with distilled water, placed in ethanol for 15 minutes, and then submerged in anhydrous toluene for 15 minutes. The cleaned tips were then placed in warm (60° C.) anhydrous toluene containing 1% 3-aminopropyltriethoxysilane (APTES) and allowed to react for 5 minutes. The tips were then removed from the APTES solution and washed with ethanol for 15 minutes. At the end of this process, the presence of amine groups on the surface of the fiber was verified by photoelectron spectroscopy.

An alginate matrix was then applied to the amine-functionalized fiber surface as follows. The immobilization matrix was a crosslinked alginate-based hydrogel, prepared by covalently crosslinking Pronova™ UP LVG alginate, selected for its low viscosity and high guluronic to mannuronic ratio, through the carboxyls with adipic acid dihydrazide (AAD) via carbodiimide chemistry. A 2% alginate solution was prepared by dissolving 1 gram of alginate in 50 mL 0.1 M MES buffer (pH 6.5) and then adding 110 mg of AAD and 79 mg of hydroxybenzotriazole (HOBt). A 0.5 mL aliquot of this solution was then mixed with 10 mg of EDC in 50 uL of MES buffer using a dual-syringe mixing technique. The total volume of the solution was approximately 0.55 mL. The alginate, AAD, HOBt, EDC mixture was then transferred to microcentrifuge vials, and the APTES-functionalized fiber tips were submerged in the alginate solution for 3-4 minutes or until the matrix began to solidify. The tips were then removed from the alginate solution, allowed to continue reacting in air for approximately 1-10 minutes, and then transferred to 0.1M, 6.5 pH MES buffer. The tips were allowed to sit in the MES buffer for 2 hours, and then they were quenched in excess phosphate buffer solution (PBS, 0.0027 M potassium chloride, 0.137 sodium chloride, pH 7.4) for a minimum of 30 minutes.

To attach the binding protein, the tips were incubated in a solution of labeled GGBP in PBS buffer [NBD-E149C/A213R/L238S GGBP] (20-60 uM, 50 uL) for several hours. The sensors were protected from ambient light during incubation. After approximately 2-8 hour of incubation, 50 uL of EDC/NHS (200 mM/50 mM) were added to the incubation tube. After 5-40 minutes, the sensor tips were removed and placed in 50 uL of 1M, pH 8.5 ethanolamine to quench the reaction. After 20 minutes in the ethanolamine solution, the sensor tips were transferred to PBS solution, where they were allowed to sit for at least 8 hours while unreacted protein diffused out. The sensors were then transferred to fresh PBS and stored in the dark until ready to use.

In a trial of the above described embodiment, the optical reader was the same as described in the previous example, with the exception that the 470 nm excitation was modulated using a solenoid-driven shutter. In addition to interfacing with and controlling the shutters and detectors, the software permitted timed acquisition of fluorescence reading, graphical display of the results, and data analysis and calibration algorithms.

Figure 7:
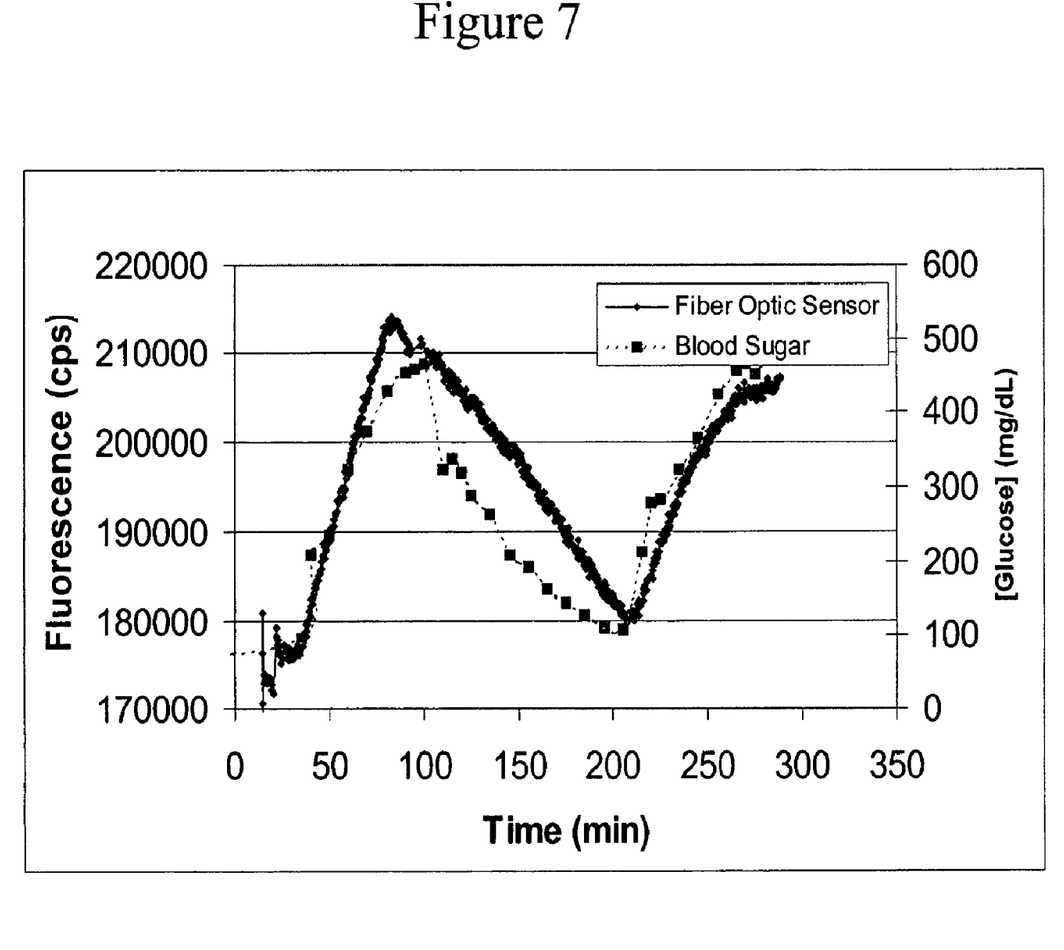
FIG. 7 shows the performance of a fiber optic biosensor according to an embodiment of the invention using a single 400 micron core fiber optic sensor and the optical configuration illustrated in FIG. 2A.

The distal end and sensing element of a biosensor formed in this manner was then inserted into the side of an anesthetized pig. Insertion was done by inserting the fiber either intradermally or subcutaneously through a hole in the skin formed by a 18-24 gauge needle. Alternating solutions of lactated ringer's with and without 10% dextrose were infused through the ear vein of the pig to increase and decrease the pig's glucose levels in a controllable fashion. At intervals, blood samples were pulled from the vena cava of the pig through a throat catheter, and blood sugar readings were tested on a handheld blood glucose meter. The fluorescence intensity of the biosensor was observed to track changing blood glucose levels in the anesthetized pig, as shown in FIG. 7.

EXAMPLE 4

In another embodiment of the invention, dual wavelength detection with an internal optical reference group was performed. The binding protein was glucose galactose binding protein (GGBP), with a cysteine substituted for a glutamic acid at position 149, an arginine substituted for an alanine at position 213 and a serine substituted for leucine at position 238 (E149C/A213R/L238S). The protein was labeled at the 149 position with the reporter group N,N'-dimethyl-N-(iodoacetyl)-N'-(7-nitrobenz-2-oxa-1,3-diazol-4-yl)ethylenediamine (IANBD amide). The reference group was Texas Red® $C_2$ maleimide attached to GGBP with a cysteine substituted for a glutamic acid at position 149 (TR-E149C GGBP). Over the physiological range of glucose concentrations, the luminescence from TR-E149C GGBP is substantially unchanged, and thus TR-E149C GGBP serves as an internal reference for the signal from the analyte-dependent binding protein and reporter group (NBD-E149C/A213R/L238S GGBP].

The biosensor was prepared by inserting the tip of a 400 micron core diameter fiber into a short piece of catheter tubing, allowing the catheter tubing to overhang the fiber tip by 0.1-0.5 mm. The fiber comprised a silica core, silica cladding, and polyimide buffer. The fiber diameter was 400/440/470 microns, where the slashes denote diameters measured from the core/cladding/buffer exteriors.

The immobilization matrix was a crosslinked alginate-based hydrogel, prepared by covalently crosslinking Pronova™ UP LVG alginate, selected for its low viscosity and high guluronic to mannuronic ratio, through the carboxyls with adipic acid dihydrazide (AAD) via carbodiimide chemistry. A 2% alginate solution was prepared by dissolving 1 gram of alginate in 50 mL 0.1 M MES buffer (pH 6.5) and then adding 110 mg of AAD and 79 mg of hydroxybenzotriazole (HOBt). The solution was stored at 4° C. until used. Using a dual-syringe mixing technique, a 0.5 mL aliquot of the alginate solution was then mixed with a 50 uL MES solution containing 10 mg of 1-ethyl-3-(3-dimethylaminopropyl) carbodiimide (EDC) and 90 μL of 60 μM TR-E149C GGBP. The alginate, AAD, HOBt, EDC, TR-E149C mixture was aspirated into a 1 mL syringe, and a blunt 30 gauge needle was attached to the syringe. The needle was primed, and then the tip was inserted into the catheter tubing mold on the optical fiber. The catheter tubing on the fiber was filled, ensuring good contact between the tip of the fiber optic and the alginate matrix. The matrix was allowed to cross-link for 15 minutes, and then the fiber tip and matrix assembly were transferred to a 0.1M, 6.5 pH MES solution, where they were stored for 2 hours. At the end of the two hours, the sensing tips were placed in excess phosphate buffer solution (PBS, 0.0027 M potassium chloride, 0.137 sodium chloride, pH=7.4) where they were stored a minimum of 30 minutes to quench the reaction.

To attach binding protein, the tips were incubated in a solution containing IANBD labeled GGBP in PBS buffer NBD-E149C/A213R/L238S GGBP. During the incubation period, the sensors were protected from ambient light. After approximately 2-8 hour of incubation, 50 uL of EDC/NHS (200 mM/50 mM) were added to the incubation tube. After 5-40 minutes, the sensor tips were removed and placed in 50 uL of 1M, pH 8.5 ethanolamine to quench the reaction. After 20 minutes in the ethanolamine solution, the sensor tips were transferred to PBS solution, where they were allowed to sit for at least 8 hours while unreacted protein diffused out. The sensors were then transferred to fresh PBS and stored in the dark until ready to use.

In a trial of the above described embodiment, the fluorescence signal was read using an optical system following the configuration illustrated in FIG. 2A. A 470 nm LED (LS-450) was used for excitation, and two single photon counting photomultiplier tubes were used as electromagnetic energy detectors. A commercial dichroic beamsplitter was used to reflect the 470 nm light from the electromagnetic energy emitter towards the fiber and to transmit the luminescence signals from the reporter and reference groups towards the detectors. A second dichroic beamsplitter was used to separate the luminescence signals from the reporter and reference groups, directing the emission from NBD-E149C/A213R/

L238S towards one detector and the emission from TR-E149C GGBP towards the other detector. A 550 nm bandpass filter in front of one detector and a 610 nm bandpass filter in front of the other detector were used to achieve further spectral resolution for NBD-E149C/A213R/L238S and TR-E149C GGBP, respectively.

Figure 8:
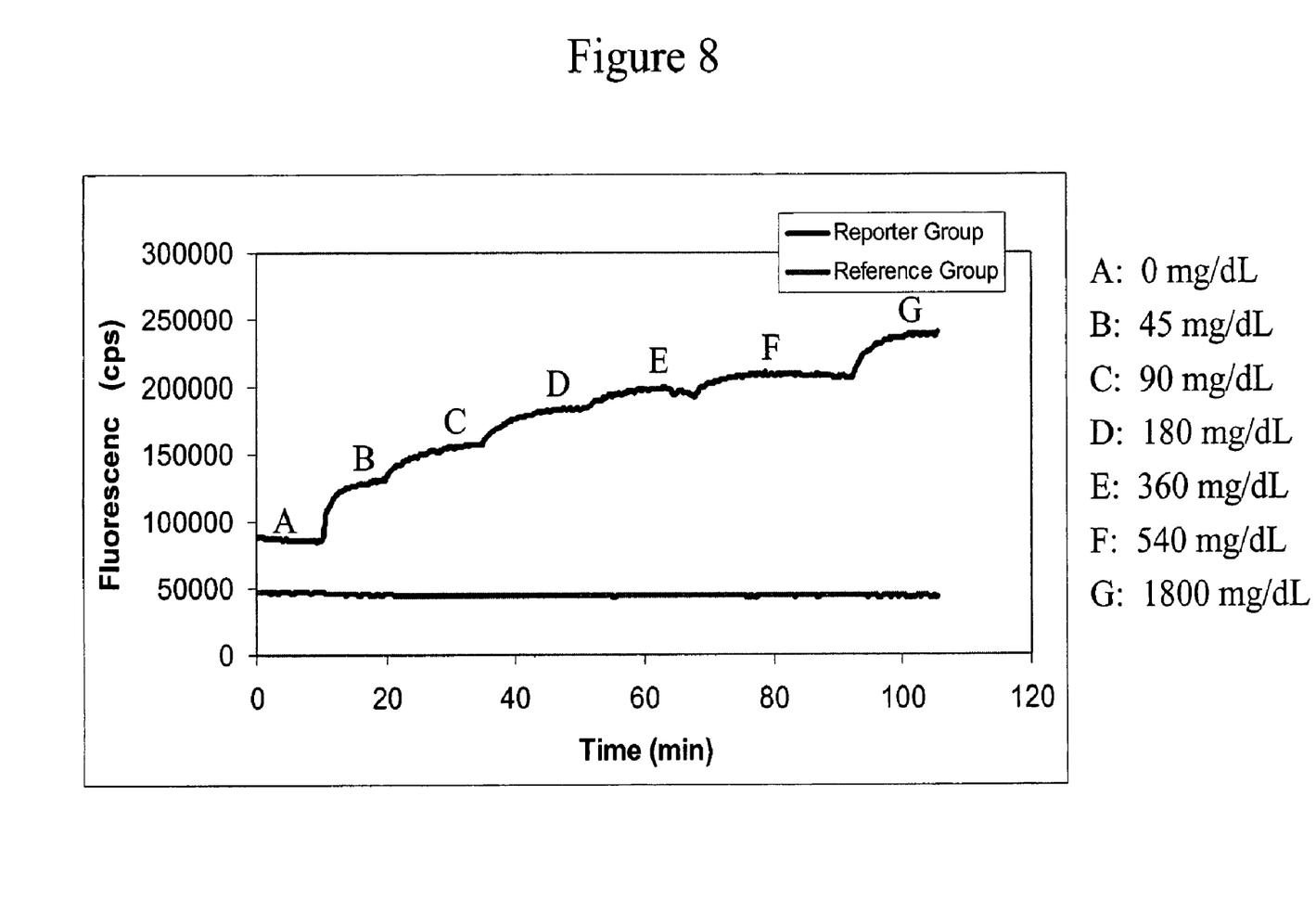
FIG. 8 illustrates an embodiment of the present invention including multiple electromagnetic energy detectors and an internal reference.

In a trial, the distal end and sensing element of a biosensor formed in this manner was inserted into solutions of PBS buffer containing different levels of glucose. Glucose levels in the solutions were measured on a clinical analyzer. FIG. 8 shows the sensor response to changing glucose levels. The 550 nm signal from the IANBD reporter group tracks changing glucose levels. The 610 nm emission from the Texas Red® reporter group is substantially unchanged as glucose levels vary. However, in this embodiment, a portion of the reporter group's emission also occurs at 610 nm. The detector in the optical system that tracks the 610 nm luminescence signal detects both the emission of the reference group and also the portion of the reporter group (IANBD) emission that occurs in this wavelength region. Since the contribution to the 610 nm signal from the reporter group is a constant fraction of the 550 nm signal, this contribution can be mathematically subtracted from the 610 nm signal to generate the signal due to the reference group alone. When this mathematical manipulation is performed, the 610 nm signal is substantially unchanging with glucose concentration as shown in FIG. 8.

While the invention herein disclosed has been described by means of specific embodiments and applications thereof, numerous modifications and variations can be made thereto by those skilled in the art without departing from the scope of the invention as set forth in the claims.

What is claimed is:

1. A device for sensing a target analyte in a sample comprising:
   (a) an optical fiber having a proximal end and a distal end;
   (b) an optical system at the proximal end of the optical fiber comprising at least one electromagnetic energy emitter and at least one electromagnetic energy detector; and
   (c) a sensing element attached to the distal end of the optical fiber and in optical connectivity with the optical fiber, the sensing element comprising (i) at least one periplasmic binding protein capable of specifically binding with at least one target analyte and at least one reporter group associated with the periplasmic binding protein and (ii) a polymeric matrix that is covalently and directly attached to said distal end of the optical fiber through reactive groups on the polymer, wherein the periplasmic binding protein and reporter group are entrapped within or attached to the polymeric matrix, wherein the matrix permits the periplasmic binding protein to retain conformational mobility, and wherein the matrix is adapted to transduce a luminescence change of the reporter group upon specific binding of the periplasmic binding protein to the target analyte.

2. The device of claim 1, further comprising a tip that houses and protects the optical fiber and the sensing element within the tip.

3. The device of claim 2, wherein the tip is selected from the group consisting of a needle and a catheter.

4. The device of claim 1, wherein the device comprises at least one reference group, and wherein the at least one reference group is associated with the at least one periplasmic binding protein.

5. The device of claim 1, wherein the sensing element is further adapted to be inserted into or through the skin of a patient.

6. The device of claim 1, wherein the periplasmic binding protein is a glucose-galactose binding protein.

7. The device of claim 1, wherein the target analyte is glucose.

8. The device of claim 1, wherein the optical fiber comprises a surface, wherein the surface of the optical fiber comprises amine groups, and wherein the reactive groups on the polymer covalently bond to the amine groups on the surface of the optical fiber.

* * * * *